United States Patent [19]

Takami et al.

[11] 4,308,064

[45] Dec. 29, 1981

[54] PHOSPHATE OF CALCIUM CERAMICS

[75] Inventors: Akio Takami, Konan; Kazuo Kondo, Nagoya, both of Japan

[73] Assignee: NGK Spark Plugs Co., Ltd., Nagoya, Japan

[21] Appl. No.: 171,409

[22] Filed: Jul. 23, 1980

Related U.S. Application Data

[62] Division of Ser. No. 84,553, Oct. 15, 1979.

[30] Foreign Application Priority Data

| Oct. 19, 1978 | [JP] | Japan | 53-127851 |
| Dec. 13, 1978 | [JP] | Japan | 53-153035 |
| Apr. 16, 1979 | [JP] | Japan | 54-46500 |

[51] Int. Cl.³ ............. C04B 35/00; A61F 1/00; A61F 5/00

[52] U.S. Cl. ............. 501/135; 3/1.9; 128/92 C; 106/35; 433/228; 501/151; 501/52; 501/1

[58] Field of Search ............. 106/45, 39.5, 39.6, 106/48, 73.1, 73.2; 128/92 C

[56] References Cited

U.S. PATENT DOCUMENTS

| 3,893,841 | 7/1975 | Nijhawan | 106/45 |
| 3,981,736 | 9/1976 | Broemer et al. | 106/39.6 |
| 4,097,935 | 7/1978 | Jarcho | 106/39.5 X |
| 4,113,500 | 9/1978 | Ebihara et al. | 106/39.5 X |
| 4,120,730 | 10/1978 | Trojer et al. | 106/39.6 |
| 4,135,935 | 1/1979 | Pfeil et al. | 106/39.6 X |
| 4,146,936 | 4/1979 | Aoyagi et al. | 427/2 |
| 4,218,255 | 8/1980 | Bajpai et al. | 106/45 |

FOREIGN PATENT DOCUMENTS 1487181 9/1977 United Kingdom ........ 106/39.5

OTHER PUBLICATIONS

Abe, Y. et al., "Studies of Calcium Phosphate Glass--Ceramics-Development of Dental Materials (Part 1)", Shikaki Kogaku-Zasshi, vol. 16, No. 36, (1975), pp. 196-198, 202.

*Primary Examiner*—Helen M. McCarthy
*Attorney, Agent, or Firm*—Wegner & Bretschneider

[57] ABSTRACT

A strong and biocompatible sintered phosphate of calcium ceramics are obtained by sintering a powdery material substantially consisting of phosphate of calcium having a Ca/P ratio of 1.4–1.75, e.g. apatite group and/or tricalcium phosphate, and not exceeding 15% by weight of $CaO-P_2O_5$ frit having a Ca/P ratio of 0.2–0.75. $Y_2O_3$ incorporation therein improves the bending strength of the ceramics. Furthermore, a $P_2O_5$-metal oxide frit wherein metal oxide being one or more selected from BaO, CaO, MgO, ZnO, NaO and $K_2O$ provides a more improved bending strength. The $Y_2O_3$ incorporation herein still improves the strength of the sintered product.

26 Claims, 1 Drawing Figure

PHOSPHATE OF CALCIUM CERAMICS

This is a division of application Ser. No. 84,553, filed Oct. 15, 1979.

BACKGROUND

The present invention relates to sintered phosphate of calcium ceramics having a high strength and density which are useful as bioceramics replaceable for bones or teeth and as dense ceramic substrates, e.g., for IC package. Phosphate of calcium, especially hydroxyapatite is bio-compatible and the sintered ceramics thereof have been proposed to be used as replacements for bones and teeth, i.e., as bio-ceramics. Due to the high density, phosphate of calcium ceramics are also useful as a substrate for IC package and a ceramic material having a high expansion coefficient similar to metal.

In the known manners for manufacturing phosphate of calcium ceramics, there have been a conventional sintering process wherein the pressed body is sintered under the atmospheric pressure, hot-press process and so on. When powdery hydroxyapatite as phosphate of calcium is sintered by said normal conventional sintering process the resultant product shows a compression strength of about 900 kg/cm$^2$ (Ceramics Japan Vol. 10 [7] 1975, P474), a low density and weak resistability against spalling, i.e. tends to spall in the course of cooling after sintering, which are counted as drawbacks of this process.

On the other hand, a compression strength of approximately 1000-2000 kg/cm$^2$ may be obtained by the hot-press process (Reports of the Institute for Medical & Dental Engineering Vol. 7, P113-118, 1973). However, this process is quite complicated, requiring an expensive apparatus cost and not susceptible of mass-production, which make a drawback of a high producing cost as a whole. In this connection the compression strength required as bone is about 4,000 kg/cm$^2$, generally.

U.S. Pat. No. 4,135,935 Pfeil et al discloses a process for sintered product wherein 20 parts by weight of precipitated fluorapatite and 34 parts by weight of $SiO_2$-$P_2O_5$-$Na_2O$-$K_2O$-$MgO$-$CaO$ glass composion is pressed, then sintered at 670° C. This glass composition comprises by weight 20-60% of $SiO_2$, 5-40% of $P_2O_5$, 2.7-20% of $Na_2O$, 0.4-20% of $K_2O$, 2.9-30% of $MgO$, and 5-40% of $CaO$. This sintered product comprises only 37% by weight of apatite, and the balance is said glass composition.

SUMMARY OF THE INVENTION

One object of the present invention is to provide a novel sintered phosphate of calcium ceramic product and a novel producing process therefor which eliminate the drawbacks in the prior art.

Another object of the present invention is to provide a ceramic phosphate of calcium product having a higher strength and density and a producing process therefor.

A further object thereof is to provide a ceramic phosphate of calcium product having a higher strength and density which is bio-compatible and replaceable for bones and teeth and a producing process therefor.

A further object thereof is to provide a strong ceramic phosphate of calcium product resistable against decomposition by lactic acid and a producing process therefor.

Still a further object thereof is to provide a strong ceramic phosphate of calcium product which may industrially easily be sintered and a producing process therefor.

Other objects, features and advantages become apparent in the detailed descriptions.

The present invention provides as a first embodiment thereof sintered phosphate of calcium ceramics which comprises 0.5-15% by weight calculated for the ceramics of $CaO$-$P_2O_5$ frit having a Ca/P atomic ratio of 0.2-0.75 and the balance of a powdery material of phosphate of calcium. The producing process thereof comprises a step of mixing said both components and a step of sintering the resultant mixture after pressing.

The present invention as a second embodiment thereof provides a ceramic phosphate of calcium product sintered by using $CaO$-$P_2O_5$ frit having a still higher strength, i.e. phosphate of calcium ceramics comprising 3-23% by weight of $Y_2O_3$ calculated for the ceramics and the balance of a powdery material substantially consisting of phosphate of calcium and $CaO$-$P_2O_5$ frit. The sintered product applying $CaO$-$P_2O_5$ frit as sintering agent to powdery phosphate of calcium achieved a bending strength of 1400 kg/cm$^2$ which approximates to that of human bone (about 1500 kg/cm$^2$). It has turned out that a still higher bending strength may be achieved by incorporating $Y_2O_3$ as a strengthening agent according to the present embodiment.

A third embodiment of the present invention further provides a sintered product with a still higher strength by applying $P_2O_5$-metal oxide frit. The phosphate of calcium ceramics provided by this embodiment comprises 0.5-15% by weight calculated for the ceramics of $P_2O_5$-metal oxide frit, which metal oxide being oxide of alkali metal, zinc and/or alkaline earth metal, and the balance of a powdery material substantially consisting of phosphate of calcium having a Ca/P atomic ratio of 1.4-1.75.

A fourth embodiment of the present invention provides the incorporation of 3-23% by weight of $Y_2O_3$ in the sintered product of the above third emodiment, which renders a still higher strength to the sintered product, realizing a bending strength exceeding 2000 kg/cm$^2$ as well as a resistability against the decomposition by lactic acid.

In the present invention, an enhanced strength of the sintered product is achieved due to a sintering effect produced by the incorporation of $CaO$-$P_2O_5$ frit or $P_2O_5$-metal oxide frit which firmly and tightly sinters the starting powdery material of phosphate of calcium.

DETAILED DESCRIPTION OF THE INVENTION

Figure 1:
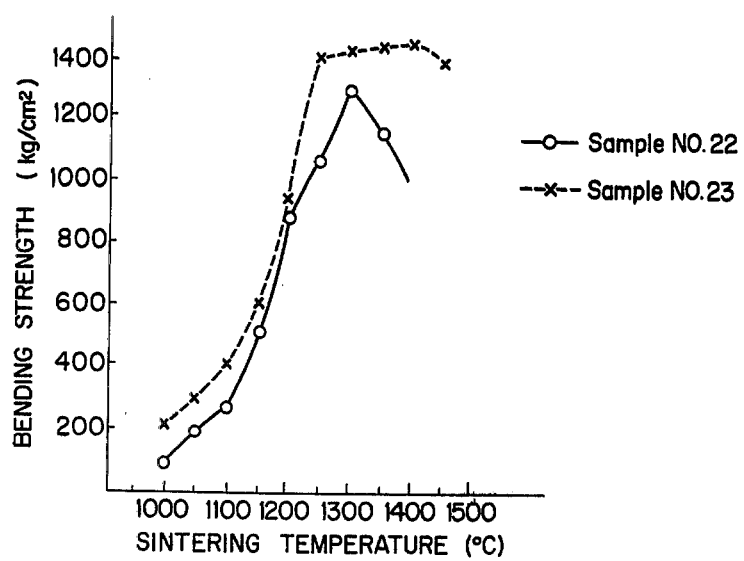
FIG. 1 graphically shows the effect of incorporation of $Y_2O_3$ in the sintered product on the optimum sintering temperature range indicating the bending strength. The samples tested correspond to Nos. 22 and 23 in Table 4, respectively.

According to the present invention, the starting base material is a powdery material substantially consisting of phosphate of calcium having a Ca/P atomic ratio of 1.4-1.75. Said powdery material substantially consists of apatite group represented by a formula (I) $Ca_5(OH, F, Cl)(PO_4)_3$ where OH, F and Cl are comprised at any ratio therebetween including zero or trace, tricalcium phosphate or a mixture thereof. Further, the powdery material may be a mixture of a major part of those as above identified and a minor part of phosphate of calcium other than apatite group and tricalcium phosphate. The apatite group encompasses synthetic or natural apatite, and preferably synthetic apatite is used. A preferred starting powdery material is synthetic hydroxyapatite, tricalcium phosphate $Ca_3(PO_4)_2$ or a mixture thereof. Conventional so-called synthetic apatite (e.g. precipitated hydroxyapatite) or synthetic (e.g. precipitated) tricalcium phosphate is composed of such mixture which may be used in the present invention.

The synthetic apatite group may be obtained through precipitation process, dry (i.e. solid state reaction) process, hydrothermal process or molten (crystallizing) process, while hydroxyapatite may be produced preferably by the precipitation process, however also by the dry or hydrothermal process. In the present invention, the term "apatite group" connotes those having a Ca/P atomic ratio of 1.4–1.75, which range encompassing the stoichiometric ratio of the apatite group substantially consisting of crystalline apatite, however, also encompassing a mixture thereof with a minor part of other Ca- or P compounds other than apatite group or tricalcium phosphate. Fluorapatite, chlorapatite or a mixture thereof may be produced if fluor and/or chlor ion are/is present in the reaction system.

The apatite group further encompasses synthetic or natural apatite group wherein Ca atom is partly replaced by Mg.

In the precipitation process, hydroxyapatite is precipitated in general from the $H_3PO_4$ aqueous solution containing Ca ion, the cake being then dried and dehydrated under an appropriate temperature, preferably 100°–150° C.

Not highly porous but relatively dense crystalline particles are preferred as the starting powdery material.

Tricalcium phosphate comprises $\alpha$- or $\beta$-tricalcium phosphate or a mixture thereof, however, preferably $\beta$-form or that comprising a major part of $\beta$- form is used. Generally, those having no anomalous crystal growth are preferred for obtaining a stronger sintered product. $\beta$-tricalcium phosphate may be prepared by heat-treating precipitated hydroxyapatite having a Ca/P atomic ratio of 1.5 at a temperature approximately 800°–1000° C.

In the dry (solid state reaction) process, the starting material may be obtained by a following manner: A mixture of phosphate of calcium such as tricalcium phosphate, calcium pyrophosphate, primary calcium phosphate (calcium dihydrogenphosphate) and the like, and calcium compound such as calcium oxide, calcium carbonate, calcium hydroxide, calcium fluoride or calcium chloride which mixture having an approximate Ca/P ratio to hydroxyapatite or tricalcium phosphate, is prepared and then heat-treated under a temperature of approximately 700°–1400° C. for crystallization.

Synthetic hydroxyapatite may be prepared by, e.g., precipitation from an aqueous $\alpha$-tricalcium phosphate solution under a controlled constant pH value, which is disclosed in Sekko Sekkai Gakkai (Gypsum and Calc Society of Japan) Summary of the 54th Scientific Lecture Meeting P10 (1977), Kadoma et al, and Summary of the 16th Yogyo Kiso-Toronkai (Ceramic Fundamental Discussion Meeting) P77 (1978), Kadoma et al.

Kanazawa et al further discloses a list of processes for producing hydroxy-, fluor- and chlorapatite, comprising precipitation-, dry-, hydrothermal- and molten process, i.e. crystallization from a molten phase, in Ceramics Japan Vol. 10(7) P463 (1975).

Kanazawa et al, ibid P464, discloses a process for preparing cristalline hydroxyapatite which comprises a step of precipitating amorphous hydroxyapatite or calcium phosphate and a further step of crystallization by aging, i.e. heat-treating the amorphous precipitation. In connection herewith, Aoki et al, ibid P473, discloses a precipitation process for obtaining amorphous hydroxyapatite of Ca/P atomic ratio of 1.4–1.67 wherein 0.5 mol/l of Ca ion and $H_3PO_4$ aqueous solution are reacted at 37° C., PH 7.1–7.4.

Aoki et al, ibid same page, also discloses a hydrothermal process wherein crystalline hydroxyapatite is obtained in an autoclave at a temperature of 125°–300° C., under a pressure of 2–85 atmospheres and at pH about 7 through hydrolysis of brushite $CaHPO_4 \cdot 2H_2O$. Aoki et al, ibid same page, further discloses a dry process for crystalline hydroxyapatite wherein $Ca_2P_2O_7$ and excess CaO are reacted under a steam flow at a temperature of 900°–1300° C.

Crystalline hydroxyapatite obtained by different types of those processes may be used as the starting material in the present invention.

According to a first embodiment of the present invention, 0.5–15%, preferably 2–10%, by weight calculated for the sintered ceramic product of a $CaO-P_2O_5$ frit having a Ca/P atomic ratio of 0.2–0.75, preferably 0.3–0.6 is admixed to the said starting powdery material. This Cao-$P_2O_5$ frit is admixed as a sintering agent. This frit may be prepared, e.g., by melting a mixture of $CaCO_3$ and $H_3PO_4$ of a predetermined Ca/P ratio, water-cooling then further finely comminuting the resultant glass product. Impurities such as $Al_2O_3$, $SiO_2$, $Na_2O$, $Fe_2O_3$, $MgO$, $B_2O_3$ which are likely to contaminate the frit during the preparation may be present in a small amount of not exceeding approximately 10 mol% calculated for the frit. The impurities from the frit does not affect on the strength of sintered ceramic product so far as the total impurities amount approximately within 0.5% by weight in the final product. For instance, a sintered product (Sample 20) comprising 5% by weight of a frit which comprises 5% by weight of $SiO_2$ exhibited no remarkable difference from that using a $SiO_2$-free frit (Sample 7).

A Ca/P atomic ratio less than or exceeding the range of 0.2–0.75 i.e. an excess in CaO or $P_2O_5$ component reduces the resultant strength of the sintered product.

0.5–15% by weight calculated for the final product of the $CaO-P_2O_5$ frit is admixed to the balance of the starting powdery material, the balance being preferably composed of synthetic hydroxyapatite, tricalcium phosphate or a mixture thereof. A preferable amount of the frit in the final product ranges approximately 2–10% by weight. If the amount of the frit therein exceeds about 15% by weight, the strength cannot be enhanced, while if the frit amount exceed about 20% by weight the strength of the sintered product become less than that obtained by sintering the single starting material only. The lowest effective amount of the frit stands about 0.5% by weight.

The improvement in the strength, especially the bending strength, depends on the incorporation of the frit as the sintering agent. Although a mixture having the same Ca/P ratio as the frit aforementioned may be prepared by mixing calcium pyrophosphate and calcium carbonate (raw frit material), a sintered product using such mixture as a sintering agent in an amount corresponding to said frit does not develop any improvement in the strength (Sample 12). An X-ray diffraction analysis of this sintered product disclosed peaks in the chart for crystalline calcium pyrophosphate and calcium carbonate, whereas no such peaks were observed in the sintered ceramics using the frit according to the present invention.

As the starting material, primary calcium phosphate, secondary calcium phosphate and calcium pyrophosphate does not develop any improvement when sintered even if the frit of the invention is admixed, and the resultant strengths are very low.

Known organic binder such as camphor preferably with diluent or solvent such as ether is admixed to the mixture of the starting powdery material and the frit, then the diluent is allowed to evaporate. The resultant mixture is then pressed into a compacted mass of a desired form then sintered under the atmospheric pressure at a temperature of approximately 1000°–1500° C., optimum sintering temperature being chosen according to the frit composition. The pressing and sintering procedures are similar also in all other embodiments of the present invention.

The ceramics of the present embodiment is useful as bioceramics e.g. replacement for bone and tooth, implant material and the like, and also as IC package substrate. Furthermore, this sintered ceramics is quite dense and has a relatively large linear expansion coefficient $\alpha = 120-140 \times 10^{-7}$° C.$^{-1}$, which features make it suitable for a composit heat-resistant material combined with metal, mounting piece for a magnetic head (e.g. made of ferrite) of VTR and tape deck, and a sealing material with a high expansion coefficient.

A second embodiment of the present invention provides a further improvement in the strength by an incorporation of $Y_2O_3$ in said sintered phosphate of calcium ceramics of the first embodiment. The incorporated amount of $Y_2O_3$ ranges in general approximately 3–23%, preferably 5–20% by weight calculated for the final product. The effect of $Y_2O_3$ incorporation appears at about 3% by weight, and excess $Y_2O_3$ more than about 24% tends to reduce the resultant strength (see Sample 26). A a source for incorporated $Y_2O_3$, oxide or other yttrium compound such as yttrium chloride ($YCl_3 \cdot H_2O$) which decomposes during a heat treatment may be used. Also any effect of $Y_2O_3$ incorporation does not appear if said mixture of pyrophosphate and calcium carbonate is employed as a starting powdery material, which is similar to the case of preceding embodiment. Namely, the present embodiment rests on the feature that $Y_2O_3$ is incorporated as the strengthening agent in said mixture of said starting powdery material substantially consisting of phosphate of calcium and $CaO-P_2O_5$ frit. Known sintering agents for phosphate of calcium such as alumina, zircon, zirconia or silica do not improve the strength of the sintered product.

Another feature attained by $Y_2O_3$ incorporation consists in that the optimum sintering temperature range is remarkably broadened in comparison to the $Y_2O_3$-free product (see FIG. 1). Thus the $Y_2O_3$ incorporation provides an advantage that the strong sintered phosphate of calcium ceramics may more easily be produced industrially.

The details how the $Y_2O_3$ incorporation affects on the improved strength is not clearly disclosed yet. However, it may be assumed that alumina, zircon, zirconia and silica would all react with phosphate of calcium or $CaO-P_2O_5$ frit resulting in crystallization of a low strength.

Still further features are provided by the $Y_2O_3$ incorporation. The decomposition rate by the lactic acid in the aqueous phase can be reduced, which makes a great advantage as the bioceramics especially for teeth. The linear expansion coefficient is $\alpha = 120-150 \times 10^{-7}$° C.$^{-1}$, which high expansion coefficient makes the ceramics also suitable for an enamel material, to say nothing of the features obtained by the first embodiment of the present invention.

Accordingly, the second embodiment realized a maximum bending strength of 1560 kg/cm$^2$ by employing $CaO-P_2O_5$ frit as the sintering agent and incorporating $Y_2O_3$.

The third embodiment of the present invention provides sintered phosphate of calcium ceramic product having a still higher strength. Here, the same starting powdery material is used. 0.5–15% by weight calculated for the final product of $P_2O_5$-metal oxide frit is admixed to said starting powdery material, then the compacted mass of the resultant mixture is sintered, which metal oxide being oxide of alkali metal, zinc and/or alkaline earth metal. A frit amount less than 0.5% by weight renders no remarkable improvement, while that exceeding 15% by weight brings no desired higher strength, thus a preferable amount of the frit ranges approximately 3–10% by weight.

The frit comprises 40–75 mol% calculated for the frit of $P_2O_5$ and 20–55 mol% of metal oxide, which oxide being one or more selected from the group consisting of BaO, CaO, MgO, ZnO, $Na_2O$ and $K_2O$ provided that the sum of $P_2O_5$ and said metal oxide is not less than 90 mole% calculated for the frit. The remaining components, i.e. impurities, of the frit may be present in an amount not exceeding 10 mol percent. Those impurities comprise $B_2O_3$, $Fe_2O_3$, $TiO_2$, $Al_2O_3$, $SiO_2$ and the like which contaminate the frit during its melting and other preparation procedures or originate from the raw material per se. Within 10 mol% of impurities in the frit, no remarkable reduction in the bending strength of the sintered product is observed, provided those total impurities do not exceed 0.5% by weight in the final sintered product.

As the metal oxide, followings are comprised in the frit in mol%: 0–55% of BaO, 0–55% of CaO, 0–20% of MgO, ZnO, $Na_2O$ and $K_2O$ respectively, provided that 20–55%, preferably 25–54%, of one or more those metal oxides is/are comprised in the frit. A frit composition which stands outside of those ranges is likely to reduce the resultant strength of the sintered product. It is preferred that not less than 20 mol% of alkaline earth metal oxide is comprised. All exemplified glass frits in Table 5 have been proved to act effectively. Alkali metal oxide is comprised preferably in an amount not exceeding 10 mol% in the frit. Alumina and silica may be comprised approximately within 10 mol% without deterioration to the product.

Either a $P_2O_5$ amount in the frit of less than 40 mol% or a metal oxide amount exceeding 55 mol% makes the frit harder to melt, thus the sintering effect would be diminished. It has turned out that when alkaline earth metal oxide is less than about 20 mol%, when alkali metal oxide is not less than about 20 mol% as a single component of the metal oxide, or when $P_2O_5$ is exceeding 75 mol%, the frit becomes unstable and hardly water-proof, i.e. the water-quenched frit is rapidly hydrated. CaO, MgO and/or ZnO incorporation affects on diminishing the decomposability by lactic acid, whereas BaO, Na$_2$O and K$_2$O incorporation affects adversely. Thus, frits comprising CaO, MgO, and/or ZnO are preferred for use in teeth replacement, wherein resistance to decomposition by lactic acid is required. However, frits comprising other components such as BaO, Na$_2$O and/or K$_2$O may also be used for other applications, such as bone replacement etc.

A quite high strength, especially bending strenth can be realized for the final product by employing the frit of the present embodiment in the above specified component, amount and manner. An elevated bending strength hereof ranges approximately 1300–1770 Kg/cm$^2$.

Furthermore, a fourth embodiment of the present invention realizes a still higher strength for the sintered product, which improvement may be attained by Y$_2$O$_3$ incorporation in the composition as disclosed in the preceding embodiment. Generally, Y$_2$O$_3$ amounts between 3–23% by weight calculated for the final product, preferably between 5–20% by weight. An amount thereof less than about 3% by weight appears not enough effective, while that exceeding about 24% remarkably diminish the strength. Here again, yttrium compound such as YCl$_3$-H$_2$O which is decomposable forming Y$_2$O$_3$ during heating may be used as Y$_2$O$_3$ source beside single yttrium oxide.

Y$_2$O$_3$ incorporation act synergetically together with the specific frit as disclosed in the preceding embodiment to elevate the strength of the product by one level to that of a bending strength exceeding 2000 kg/cm$^2$. Y$_2$O$_3$ further improves the toughness of the product as well as broadens the optimum sintering temperature range to realize a highest strength for one specified composition in comparison with the case of non Y$_2$O$_3$ incorporation, which effects are similar to the case where the CaO-P$_2$O$_5$ type frit is used. Accordingly, the strong phosphate of calcium ceramic product can be sintered more easily by the Y$_2$O$_3$ incorporation in the industrial practical production.

The product of the present embodiment containing Y$_2$O$_3$ and sintered with said P$_2$O$_5$-metal oxide frit has a less decomposability by lactic acid. Linear expansion coefficient $\alpha = 120\text{--}140 \times 10^{-7\circ}$ C.$^{-1}$ was measured for the products by the third and fourth embodiment. Other features and advantages are also realized by these embodiments as well as by the foregoing first and second embodiments.

Any known procedures or steps may be done or added for completing the embodiments as disclosed hereinabove without departing from the scope of the present invention.

The present invention is further illustrated by the following Examples without limiting the invention thereto.

EXAMPLES

EXAMPLE 1

A fine powdery CaO-P$_2$O$_5$ frit was prepared by mixing H$_3$PO$_4$ and CaCO$_3$ so that the resultant mixture has a Ca/P atomic ratio of 0.3–0.6, melted in a platinum crucible for about 2 hours at a temperature of 1300°–1400° C., the resultant molten mass being water-quenched, then finely comminuted into a mean particle diameter of about 5–6$\mu$.

A hydroxyapatite starting material having a Ca/P atomic ratio of 1.68 was prepared by a precipitation process. From a mixture aqueous solution of H$_3$PO$_4$ and Ca(OH)$_2$ aqueous slurry, hydroxyapatite was precipitated under the room temperature. The precipitated cake was then dehydrated at a temperature between 100°–150° C. forming a powdery material having average particle diameter of about 4.5$\mu$ and an absolute specific gravity of 2.70. The crystal showed hexagonal system.

Tricalcium phosphate substantially consisting of $\beta$-form was synthetically prepared from precipitated hydroxyapatite having a Ca/P atomic ratio of 1.50 by heat-treating said precipitation at a temperature of 800°–1000° C.

The frit was admixed in a predetermined amount to the resultant hydroxyapatite, $\beta$-tricalcium phosphate and a mixture thereof, respectively, as the starting powdery base material. 300 g of each resultant mixture was thoroughly wet-mixed, then 3% by weight (9 g) of camphor as an organic binder together with an optimum amount (300 ml) of ether was admixed thereto. After ether was allowed to evaporate, the resultant mixture was compressed under a pressure of 800 kg/cm$^2$ into shaped bodies having a dimension of 12 mm wide $\times$ 40 mm long $\times$ 4 mm thick. Then the pressed bodies were heated at a temperature elevation rate of 300° C./hour, and each pressed body was sintered at a different stepwise temperature with an interval of 50° C. between 1000° and 1500° C. for one hour. For the resultant sintered samples were measured the bending and compression strength and observed the external appearance as well as structure. Those samples having the highest bending strength among those obtained by different sintering temperatures are listed in Table 1 and 2.

The samples containing 5–10% by weight of the frit showed a significant improvement in the bending strength and no spalling, whereas the sample (No.1) which is a reference test, comprising no frit showed a lower bending strength of 800 kg/cm$^2$ and a relatively weak resistivity against the spalling on cooling after sintered. The compression strength are not shown in Table 1, however, the compression strength for the same samples showed approximately 3–4 times of the bending strength, e.g. Sample No.4 showed that of about 4 times thereof. The X-ray diffraction analysis was made for the samples having the high bending strength and disclosed that the major components of the sintered samples were a mixture of hydroxyapatite, $\beta$- and $\alpha$- tricalcium phosphate (3CaO-P$_2$O$_5$). The optimum sintering temperature at which a highest bending strength was obtained, e.g., for Sample 7 was around 1300° C. The bending strength was measured by three points bending test having a span of 20 mm for the sample pieces of said dimension after polishing the surface. The same testing procedures were applied in the all Examples as disclosed hereinafter.

EXAMPLE 2

(Sample 20)

A frit comprising 0.08 molar parts of SiO$_2$ as a contamination and the balance of 1.2 molar parts of CaO-P$_2$O$_5$ (Ca/P atomic ratio: 0.6) was prepared substantially in the same manner as in Example 1. Sintered samples were obtained by using this frit in the same manner as in Example 1. Samples having the highest bending strength among those sintered at different temperatures are shown in Table 2. No remarkable differences were observed between these and those containing no SiO$_2$ as disclosed in Example 1.

REFERENCE TEST 1

(Sample 12-15)

a. (Sample 12)

Hydroxyapatite as disclosed in Example 1 was used as a starting base material. This base material and a mixture of calcium pyrophosphate and calcium carbonate having a Ca/P atomic ratio of 0.6 in place for said frit were mixed in predetermined ratios, then the sintered samples were prepared in the same manner as in Example 1. The result is shown in Table 1. The bending strength obtained showed a far lower one in comparison with that for sample 7 of Example 1. An X-ray diffraction analysis disclosed peaks for calcium pyrophosphate and calcium carbonate in the chart.

b. (Samples 13-15)

Primary and secondary calcium phosphate and calcium pyrophosphate were employed as a starting base material, and the frit as disclosed in Example 1 was admixed thereto then sintered samples were obtained in the same manner hereinafter as in Example 1. The resultant samples showed only a very low bending strength, also a crack formation in the surface was observed in Sample 15.

EXAMPLE 3

(Samples 23-26, 32, 33)

(a) A fine powdery $CaO-P_2O_5$ frit having Ca/P atomic ratio of 0.6 and a mean particle diameter of around 5-6$\mu$ was prepared in the same manner as disclosed in Example 1. The hydroxyapatite, tricalcium phosphate and a mixture thereof having a mean particle diameter of about 4.5$\mu$ as disclosed in Example 1 were used as a starting powdery base material.

The starting base material, the frit and $Y_2O_3$ were throughly mixed in predetermined ratios, then sintered samples were prepared hereinafter in the same manner as in Example 1. Those samples which showed the highest bending strength among different heating temperatures are listed in Table 4. Whereas $Y_2O_3$-free Sample 22 was prepared for comparative purpose.

A relation between the sintering temperature and the resulting bending strength for the $Y_2O_3$-incorporated sample (23) is shown in FIG. 1 in comparison with a $Y_2O_3$-free sample (22). FIG. 1 exhibits a broadened sintering temperature range for an optimum sintering. Other samples containing $Y_2O_3$ showed also the same features. Furthermore, the samples (23-25) containing $Y_2O_3$ improved in their bending strength in comparison to the $Y_2O_3$ free sample (22).

(b) The resistivity against the decomposition by lactic acid was tested for Samples 21, 22 and 24, the results being shown in Table 3. The test was carried out in a following way; A fine powder through 250 mesh prepared by comminuting each sample was dipped in a lactic acid aqueous solution at pH 4.0 and allowed to stand for 20 hours at 37° C., then dissolved Ca ion in the resulting solution was determined by atomic absorption spectroscopy.

TABLE 3

| Sample No. | Dissolved Ca ion in lactic acid solution at pH 4 (ppm) | Remarks |
|---|---|---|
| 21 | 8.2 | hydroxyapatite (H . Ap) |
| 22 | 9.6 | H . Ap:frit = 95:5, Ca/P = 0.6 |
| 24 | 6.0 | H . Ap:frit:$Y_2O_3$ = 85:6:9 |
| Reference | 8.8 | natural apatite of human jaw bone* |

*Note:
Aoki et al, Shikai Tenbo (Review Dental World) Vol. 49. P569, 4 (1977)

TABLE 1

| Sample No. | Base material | (wt. parts) | Sintering agent Ca/P ratio | wt. parts | Bending str. kg/cm$^2$ | Remarks (nc: not claimed, r: ref. test) |
|---|---|---|---|---|---|---|
| 1 | H . Ap | 100 | — | — | 800 | r  low spalling-resistivity |
|   |   |   |   |   |   | nc H . Ap: hydroxyapatite |
| 2 | " | 95 | 0.3 | 5 | 1250 |   |
| 3 | " | 80 | " | 20 | 700 | nc |
| 4 | " | 95 | 0.45 | 5 | 1400 |   |
| 5 | " | 90 | " | 10 | 950 |   |
| 6 | " | 80 | " | 20 | 750 | nc |
| 7 | " | 95 | 0.6 | 5 | 1300 |   |
| 8 | " | 90 | " | 10 | 1000 |   |
| 9 | " | 80 | " | 20 | 750 | nc |
| 10 | TCP | 95 | 0.45 | 5 | 1000 | TCP: Tricalcium phosphate |
| 11 | H . Ap / TCP | 50 / 45 | " | 5 | 1300 |   |
| 12 | H . Ap | 95 | 0.6* | 5 | 850 | nc *mixture of CPP** & CaCO$_3$ |
| 13 | PCP | 95 | 0.6 | 5 | 250 | nc PCP: prim. calcium phosphate |
| 14 | SCP | 95 | 0.6 | 5 | 220 | nc SCP: sec. calcium phosphate |
| 15 | CPP** | 95 | 0.6 | 5 | 200 | nc cracks in surface **CPP: Ca-pyrophosphate |

TABLE 2

| Sample No. | Base material | (wt. Parts) | Sintering agent Ca/P ratio | wt. parts | Bending str. kg/cm$^2$ | Remarks |
|---|---|---|---|---|---|---|
| 16 | H . Ap | 85 | 0.45 | 15 | 880 |   |
| 17 | " | 85 | 0.60 | 15 | 920 |   |
| 18 | " | 95 | 0.2 | 5 | 1000 |   |
| 19 | " | 95 | 0.75 | 5 | 1150 |   |
| 20 | " | 95 | 0.6* | 5 | 1280 | *1.2 CaO . P$_2$O$_5$ . 0.08 SiO$_2$ |

EXAMPLE 4

(Sample 27-29)

Samples were prepared by using frits having Ca/P atomic ratios of 0.3 and 0.45, otherwise in the same manner as in Example 3 in comparison between $Y_2O_3$ containing and $Y_2O_3$-free samples. Remarkable effect of $Y_2O_3$ incorporation was exhibited.

EXAMPLE 5

(Samples 30-31)

β-tricalcium phosphate was used as a starting powdery base material in place for hydroxy-apatite. Thus sintered samples were prepared otherwise in the same manner as in preceding Example. The effects of $Y_2O_3$ incorporation were clearly observed.

REFERENCE TEST 2

(Sample 2).

Single hydroxyapatite was sintered without adding frit and $Y_2O_3$ in a similar way as in Example 1.

EXAMPLE 6

Step 1

(a) Frit Samples A-R as listed in Table 5 were prepared by melting mixtures comprising $H_3PO_4$, $BaCO_3$, $CaCO_3$, $MgCO_3$, ZnO, $Na_2CO_3$, $K_2CO_3$, $Al_2O_3$ and/or $SiO_2$ so that the compositions thereof become those for Samples A-R as listed in Table 5. The melting and other procedures were carried out in the same manner as in Example 1. The particular characteristics of the resultant frits are shown in Table 5.

Step 2

(a) Sintered products were prepared by using the frits A-G of Step 1 and the balance of the starting base material as in Example 1 in predetermined compositions as listed in Table 6. The other preparing procedures were the same as in Example 1. The results are shown in Table 6.

(b) Sintered products were prepared by using 5% by weight of frits H-R, respectively, and the balance of hydroxyapatite as in Example 1 in the same manner as preceding paragraph (a). The results are shown in Table 5.

(c) $Y_2O_3$ was further incorporated in the composition system as disclosed in Step 2 (a). The results are shown in Table 6. (Sample 53).

TABLE 4

| Sample No. | Base material | wt. parts | Frit Ca/P ratio | Frit wt. parts | Strengthening agent | wt. parts | Bending str. (kg/cm²) | Remarks |
|---|---|---|---|---|---|---|---|---|
| 21 | H . Ap* | 100 | — | — | — | — | 800 | hardly spalling resistable not claimed |
| 22 | " | 95 | 0.6 | 5 | — | — | 1300 | |
| 23 | " | 85 | 0.6 | 9 | $Y_2O_3$ | 6 | 1405 | |
| 24 | " | 85 | 0.6 | 6 | " | 9 | 1560 | |
| 25 | " | 70 | 0.6 | 12 | " | 18 | 1360 | |
| 26 | " | 70 | 0.6 | 6 | " | 24 | 850 | not claimed |
| 27 | " | 95 | 0.3 | 5 | — | — | 1250 | |
| 28 | " | 85 | 0.3 | 6 | $Y_2O_3$ | 9 | 1350 | |
| 29 | " | 85 | 0.45 | 6 | " | 9 | 1450 | |
| 30 | TCP** | 85 | 0.6 | 6 | " | 9 | 1500 | |
| 31 | " | 95 | 0.6 | 5 | — | — | 1000 | |
| 32 | H . Ap | 92 | 0.6 | 5 | $Y_2O_3$ | 3 | 1320 | |
| 33 | " | 70 | 0.6 | 9 | " | 21 | 1310 | |

Notes:
*H . Ap: Hydroxyapatite
**TCP: Tricalcuim phosphate

TABLE 5

| Frit No. | Composition of Frit (mol%) | | | | | | | | | Characteristics of frit | | Bending strength of sintered product (kg/cm²) |
|---|---|---|---|---|---|---|---|---|---|---|---|---|
| | $P_2O_5$ | BaO | CaO | MgO | ZnO | $Na_2O$ | $K_2O$ | $Al_2O_3$ | $SiO_2$ | Tg °C | Expansion coefficient $\alpha \times 10^{-7}$ °C$^{-1}$ (30-500 °C.) | |
| A | 46 | 32 | 20 | | | | | | | 525 | 120 | |
| B | 46 | 47 | — | 7 | | | | | | 525 | 150 | |
| C | 42 | — | 44 | | 9 | | | | | 507 | 130 | |
| D | 60 | 20 | 5 | 5 | | | 5 | 5 | | 510 | 100 | |
| E | 43 | 3 | 40 | 2 | | 10 | | | | 505 | 102 | |
| F | 47 | 3 | 49 | | | | | 1 | | 535 | 120 | |
| G | 70 | 10 | | 10 | 5 | | | 5 | | 640 | 80 | |
| H | 70 | 10 | | 20 | | | | | | 560 | 78 | 1300-1600 |
| I | 60 | 20 | | | 20 | | | | | 530 | 100 | 1300-1600 |
| J | 45 | 15 | 20 | | | | 20 | | | 520 | 112 | 1300-1600 |
| K | 45 | 15 | 20 | | | 20 | | | | 515 | 120 | 1300-1600 |
| L | 60 | 15 | | 5 | 5 | 5 | | 9 | 1 | 520 | 93 | 1300-1600 |
| M | 50 | 37 | | 3 | | | | 2 | 8 | 490 | 130 | 1300-1600 |
| N | 45 | 30 | 15 | $B_2O_3$ 5 | $Fe_2O_3$ 1 | $TiO_2$ 1 | | 2 | 1 | 510 | 128 | 1300-1600 |
| O | 47 | 2.5 | 49.5 | | | | | | 1 | 520 | 114 | 1710 |
| P | 46 | 47 | | 5 | | | 2 | | | 488 | 150 | 1630 |
| Q | 47 | 7.5 | 44.5 | | | | | | 2 | 498 | 122 | 1450 |
| R | 46 | 12 | 40 | | | | | | 2 | 513 | 121 | 1330 |

TABLE 5A

| Frit No. | Composition of Frit (% by weight) | | | | | | | | | | Characteristics of frit | | Bending strength of sintered product (kg/cm²) |
|---|---|---|---|---|---|---|---|---|---|---|---|---|---|
| | $P_2O_5$ | BaO | CaO | MgO | ZnO | $Na_2O$ | $K_2O$ | $Al_2O_3$ | $SiO_2$ | Tg °C. | Expansion coefficient $\alpha \times 10^{-7}$ °C.$^{-1}$ (30–500° C.) | |
| A | 51.2 | 38.5 | 8.8 | | | | | 1.5 | | 525 | 120 | |
| B | 46.6 | 51.4 | — | 2.0 | | | | | | 525 | 150 | |
| C | 67.6 | — | 25.0 | | 7.4 | | | | | 507 | 130 | |
| D | 65.3 | 23.5 | 2.2 | 1.5 | | | 3.6 | 3.9 | | 510 | 100 | |
| E | 63.4 | 4.78 | 23.3 | 0.83 | | 6.44 | | | 1.25 | 505 | 102 | |
| F | 66.85 | 4.60 | 27.53 | | | | 1.02 | | | 535 | 120 | |
| G | 77.69 | 11.99 | | 3.15 | 3.18 | | | 3.99 | | 640 | 80 | |
| H | 80.94 | 12.50 | 6.56 | | | | | | | 560 | 78 | |
| I | 64.47 | 23.21 | | | 12.32 | | | | | 530 | 100 | |
| J | 54.63 | 19.67 | 9.59 | | | | 16.11 | | | 520 | 112 | 1300–1600 |
| K | 57.81 | 20.82 | 10.15 | | | 11.22 | | | | 515 | 120 | |
| L | 66.15 | 17.87 | | 1.57 | 3.16 | | 3.66 | 7.13 | 0.46 | 520 | 93 | |
| M | 52.28 | 41.79 | | 0.89 | | | | 1.50 | 3.54 | 490 | 130 | |
| N | 49.14 | 35.39 | 6.48 | $B_2O_3$ 5.52 | $Fe_2O_3$ 0.48 | $TiO_2$ 0.96 | | 1.57 | 0.46 | 510 | 128 | |
| O | 67.45 | 3.88 | 28.07 | | | | | | 0.6 | 520 | 114 | 1710 |
| P | 46.17 | 50.96 | | 1.43 | | | 1.44 | | | 488 | 150 | 1630 |
| Q | 63.92 | 11.02 | 23.91 | | | | | | 1.15 | 498 | 122 | 1450 |
| R | 60.37 | 17.0 | 20.74 | | | | | | 1.89 | 513 | 121 | 1330 |

The solubility in the lactic acid solution was tested, the results being the same as those in Table 3.

TABLE 6

| Sample | Base material | | Frit | | Bending strength kg/cm² | Remarks |
|---|---|---|---|---|---|---|
| | | wt. parts | | wt. parts | | |
| 41 | H . Ap | 100 | — | 0 | 800 | not claimed hardly spalling-resistable |
| 42 | " | 95 | A | 5 | 1770 | |
| 43 | " | 95 | B | 5 | 1630 | |
| 44 | " | 95 | C | 5 | 1600 | |
| 45 | " | 95 | D | 5 | 1350 | |
| 46 | " | 95 | E | 5 | 1300 | |
| 47 | " | 95 | F | 5 | 1730 | |
| 48 | " | 95 | G | 5 | 1200 | |
| 49 | " | 90 | A | 10 | 1300 | |
| 50 | " | 80 | A | 20 | 500 | not claimed |
| 51 | TCP | 95 | A | 5 | 1650 | |
| 52 | H . Ap50 TCP50 | 95 | A | 5 | 1580 | |
| 53 | H . Ap86 $Y_2O_3$9 | 95 | A | 5 | 2050 | |

Notes:
H . Ap; hydroxyapatite,
TCP; tricalcium phosphate (")

We claim:

1. Phosphate of calcium ceramics obtained by sintering a ceramic material consisting essentially of 3–23% by weight of $Y_2O_3$, 0.5–15% by weight of $CaO-P_2O_5$ frit having a Ca/P atomic ratio in the range of 0.70–0.75, both calculated for the ceramics, and the balance of a powdery material substantially consisting of phosphate of calcium having a Ca/P atomic ratio of 1.4–1.75, and being of improved bending strength over ceramics otherwise the same but not containing $Y_2O_3$.

2. The ceramics of claim 1 wherein said powdery material substantially consisting of phosphate of calcium is apatite group, tricalcium phosphate or a mixture thereof.

3. The ceramics of claim 2 wherein said apatite group is synthetic or natural apatite or a mixture thereof.

4. The ceramics of claim 3 wherein said apatite group essentially consists of apatite represented by a formula $Ca_5(OH, F, Cl)(PO_4)_3$.

5. The ceramics of claim 4 wherein said apatite group is a synthetic apatite produced by precipitation process, dry process, hydrothermal process or molten process, or a mixture of said synthetic apatites.

6. The ceramics of claim 2 wherein said apatite group is synthetic hydroxyapatite having a Ca/P atomic ratio of 1.4–1.75 produced by precipitation process, dry process or hydrothermal process.

7. The ceramics of claim 1 wherein said powdery material substantially consisting of phosphate or calcium is hydroxyapatite, tricalcium phosphate or a mixture thereof.

8. The ceramics of claim 1 wherein said $CaO-P_2O_5$ frit comprises approximately 0–10 mol% calculated for the frit of $SiO_2$ and/or $Al_2O_3$ and the balance of CaO and $P_2O_5$.

9. The ceramics of claim 1 wherein the ceramics comprise impurities not exceeding approximately 0.5% by weight calculated for the ceramics originating from the frit, which impurities comprise $SiO_2$, $Al_2O_3$, $B_2O_3$, $TiO_2$ and/or $Fe_2O_3$.

10. The ceramics of claim 1, obtained by sintering the ceramic material at approximately 1000°–1500° C.

11. The ceramics of claim 1, wherein said frit is prepared by melting the components of said frit at approximately 1300°–1400° C., then comminuting the resultant frit.

12. The ceramics of claim 1, wherein the oxide or chloride of yttrium or mixture thereof is used as a source for $Y_2O_3$.

13. Phosphate of calcium ceramics obtained by sintering a ceramic material consisting essentially of 3–23% by weight of $Y_2O_3$, 0.5–15% by weight of $P_2O_5$-metal oxide frit, both calculated for the ceramics, and the balance of a powdery material consisting essentially of phosphate of calcium having a Ca/P atomic ratio of 1.4–1.75, the $P_2O_5$-metal oxide frit consisting essentially of, in mol% calculated for the frit, 40–75% $P_2O_5$ and 20–55% of one or more metal oxide selected from the group consisting of BaO, CaO, MgO, ZnO, $Na_2O$ and $K_2O$, provided that the sum of said $P_2O_5$ and said metal oxide is not less than 90 mol% in the frit and said $P_2O_5$-metal oxide frit in mol% comprises 0–55% BaO, 0–55% CaO, 0–20% MgO, 0–20% ZnO, 0–20% $Na_2O$ and 0–20% $K_2O$, and being of improved bending strength over ceramics otherwise the same but not containing $Y_2O_3$.

14. The ceramics of claim 13, wherein the metal oxide in said frit consists essentially of CaO.

15. The ceramics of claim 14, wherein said frit consists essentially of $P_2O_5$ and CaO.

16. The ceramics of claim 13 wherein said powdery material substantially consisting of phosphate of calcium is apatite group, tricalcium phosphate or a mixture thereof.

17. The ceramics of claim 16 wherein said apatite group is synthetic or natural apatite or a mixture thereof.

18. The ceramics of claim 17 wherein said apatite group essentially consists of apatite represented by a formula $Ca_5(OH, F, Cl)(PO_4)_3$.

19. The ceramics of claim 18 wherein said apatite group is synthetic apatite produced by precipitation process, dry process, hydrothermal process or molten process, or a mixture of said synthetic apatites.

20. The ceramics of claim 16 wherein said apatite group is synthetic hydroxyapatite having a Ca/P atomic ratio of 1.4–1.75 produced by precipitation process, dry process or hydrothermal process.

21. The ceramics of claim 13 wherein said powdery material substantially consisting of phosphate of calcium is hydroxyapatite, tricalcium phosphate or a mixture thereof.

22. The ceramics of claim 13 wherein said $P_2O_5$-metal oxide further frit comprises approximately 0–10 mol% calculated for the frit of $SiO_2$ and/or $Al_2O_3$ and the balance of CaO and $P_2O_5$.

23. The ceramics of claim 13 wherein the ceramics comprise impurities not exceeding approximately 0.5% by weight calculated for the ceramics originating from the frit, which impurities comprise $SiO_2$, $Al_2O_3$, $B_2O_3$, $TiO_2$ and/or $Fe_2O_3$.

24. The ceramics of claim 13, obtained by sintering the ceramic material at approximately 1000°–1500° C.

25. The ceramics of claim 13, wherein said frit is prepared by melting the components of said frit at approximately 1300°–1400° C., then comminuting the resultant frit.

26. The ceramics of claim 13, wherein the oxide or chloride of yttrium or a mixture thereof is used as a source for $Y_2O_3$.

* * * * *